United States Patent
Lewis et al.

(10) Patent No.: US 7,029,608 B1
(45) Date of Patent: Apr. 18, 2006

(54) IRIS ASSEMBLY FOR A PROSTHETIC EYE DEVICE

(76) Inventors: Frederick R. Lewis, 1360 Bluesail Cir., Westlake Village, CA (US) 91361; Carole Lewis Stolpe, 4239 Navajo St., Toluca Lake, CA (US) 91602

( * ) Notice: Subject to any disclaimer, the term of this patent is extended or adjusted under 35 U.S.C. 154(b) by 546 days.

(21) Appl. No.: 10/192,958

(22) Filed: Jul. 11, 2002

(51) Int. Cl.
*B29D 11/00* (2006.01)

(52) U.S. Cl. .......................................... 264/1.7; 156/61

(58) Field of Classification Search ................ 623/4.1, 623/6.64; 156/61; 264/1.1, 1.7, 1.32
See application file for complete search history.

(56) References Cited

U.S. PATENT DOCUMENTS

| 2,497,873 | A | * | 2/1950 | Erpf ........................... 623/6.64 |
| 5,863,363 | A | * | 1/1999 | Sankey ........................ 156/61 |
| 6,746,120 | B1 | * | 6/2004 | Broderick et al. .......... 351/177 |
| 6,811,461 | B1 | * | 11/2004 | Maddocks et al. .......... 446/392 |
| 2004/0233383 | A1 | * | 11/2004 | Sandler et al. .............. 351/163 |
| 2005/0067725 | A1 | * | 3/2005 | Hsu ........................... 264/1.32 |
| 2005/0272833 | A1 | * | 12/2005 | Doshi .......................... 523/160 |

* cited by examiner

*Primary Examiner*—Suzette J-J Gherbi
(74) *Attorney, Agent, or Firm*—Eley Law Firm Co.; James R. Eley; Michael A. Forhan (57) ABSTRACT

An iris assembly of this invention comprises an iris button having a frontside surface. An iris member is joined to the iris button frontside surface and has an iris image disposed thereon. The iris image is provided using digital image capture, storage, enhancement, and printing techniques, and is provided onto a suitable substrate. A cornea piece is made from a clear material, and is joined to the iris member frontside surface. Prior to joining, the iris member is encapsulated with a clear protective film thereover that operates to protect the iris image from unwanted smudging or other type of distortion during the step of joining the cornea piece. Iris assemblies of this invention are constructed in a manner that provide a more accurate reproduction of the iris image, in a manner that is both time efficient and cost effective, when compared to conventional iris assemblies and methods for making the same.

13 Claims, 4 Drawing Sheets

IRIS ASSEMBLY FOR A PROSTHETIC EYE DEVICE

FIELD OF THE INVENTION

This invention relates to an iris assembly as used with a prosthetic eye device and, more particularly, to an iris assembly and method of making the same that uses digital imaging, enhancing, storing, and printing techniques; image encapsulation techniques; and special curing techniques for the purpose of providing an iris assembly having a matching appearance of a natural eye in a manner that is time and cost efficient.

BACKGROUND

Prosthetic eye devices are known in the art, and can be configured to partially or completely replace an eye, e.g., a human eye for the purpose or providing a more normal appearance. People can require use of such prosthetic eye device for a variety of reasons, such as by an accident, disease or birth defect. Thus, the type of prosthetic eye device that is used can and will vary in its design depending on the particular application. In the case where the entire eye is being replaced, or a case where a frontside portion of the existing eye is being complemented, the prosthetic eye device can include an iris portion that is constructed to replicate the appearance of a natural eye, e.g., to replicate the appearance of the patient's existing iris. The iris portion of the device comprises a complex colored and patterned portion that extends concentrically around the pupil portion of the eye to the sclera or white portion of the eye.

Prosthetic eye devices, e.g., in the form of a replacement or artificial eye, are conventionally made from materials such as methyl methacrylate, and comprise an iris assembly positioned at a frontside portion of the eye device that replicates the color and patterning of a natural eye. The iris assembly is formed from a composite construction of individual elements. Typically, the iris image, depicting the complex color and patterning of the eye, is provided on a flat disk-shaped rigid plastic element.

The most difficult and time consuming part of making a prosthetic eye device comprising an iris assembly is duplicating the iris, as humans have a complex multicolored and patterned iris that can vary significantly. To achieve realistic color and pattern matching, it has been the conventional practice to make the entire iris image by the time consuming practice of painting the color and pattern of the iris (in a manner matching the person's existing eye) onto the piece of plastic by hand. In order to obtain the desired color intensity of the iris, oil-based paints are used or mixed with acrylic paints.

An alternative method of replicating the iris portion of the eye for use in a prosthetic eye device involves a process of printing onto a flat sheet of photographic film of photographic paper a basic color of an iris. In this method, the basic color of an iris is printed (by screen printing technique) onto the flat piece of photographic film or paper as a starting point, and the film or paper is placed on a flat disk-shaped plastic element. The basic color is selected to generally match the underling color of the patient's iris. The desired iris image matching the patient's eye, comprising the complex arrangement of coloring and patterning, is then provided by hand painting over the printed base color. This method was thought useful, for potentially minimizing the amount of hand painting required during iris assembly formation, by providing a basic colored starting point.

While the above-described photographic technique was helpful in reducing the amount of time necessary to create the iris image, by reducing the amount of initial hand painting, this technique is not without its problems. For example, during subsequent steps in making the prosthetic eye device, the iris image can become distorted. This occurs because the subsequent processing steps involved in making a prosthetic eye device involves exposing the iris image to adhesives having strong solvents. The presence of these solvents is known to cause the image captured on photographic film or photographic paper to be dissolved.

There are many known disadvantages to the above-described conventional methods of making the iris assembly for use in a prosthetic eye device. A first disadvantage relates to the current practice of placing the iris image onto a flat substrate, e.g., a disk-shaped plastic element, whether the iris image is created entirely by hand painting or by the hybrid process of hand painting over the printed base color. In either technique, the iris image is flat and placed on a flat substrate. In many applications, the prosthetic eye device is made to complement an existing portion of a patent's eye or an ocular implant. This type of fitment often requires that a backside surface portion of the prosthetic eye device, e.g., a portion that includes a backside surface of the iris assembly, be configured having a nonplanar, e.g., a concave geometry. Conventional iris assemblies comprising an iris image placed on a flat or planar substrate is not well suited for this type of prosthetic eye device application because they do not permit surface shaping. Another disadvantage associated with conventional iris assemblies comprising a flat iris image is that, while appearing normal from a front-facing view, the iris image does not appear normal looking from a side view.

Another known disadvantage, associated with the above-described methods of making an iris assembly, relates to the current practice of having to paint either the entire iris image, or a portion of the iris image, by hand. Since the color and pattern of a person's iris is complex and different, the process of painting the entire iris image by hand involves a time consuming practice of starting from scratch each time. The time spent in creating the desired iris image is reduced somewhat by using the photographic technique. However, because the photographic technique still involves some amount of hand painting, it is still time consuming. Additionally, in either technique, once the iris image is painted it may take many iterative steps of modifying the initial image to perfect the look of the iris in the completed iris assembly. Oftentimes it is less time consuming to start from scratch rather than to modify an existing image.

Another disadvantage relates to the current practice of using oil-based paints to provide the desired iris color intensity. It is known that the use of such oil-based paints have a coefficient of expansion that is different than that of the surrounding monomeric or polymeric materials that are used to form the remaining members of the iris assembly. Because a prosthetic eye device is exposed to moisture when worn, and repeated cycles of being wet and dry, it is theorized that the different coefficients of expansion between the adjacent members in the iris assembly are responsible for delamination of such members, whereby the painted paper member becomes separated from adjacent iris assembly members. This delamination is not desired as it makes the iris portion of the eye appear cloudy or distorted, ultimately requiring replacement.

Another disadvantage also relates to the current practice of hand painting the iris image and using oil-based paints to provide the desired iris color and pattern onto the plastic element. During the process of making the iris assembly, after the iris image is painted on the plastic element, a clear lens cover or cornea piece is placed over and adhered to the painted surface of the plastic element using a suitable adhesive. During the step of adhering the front cover to the iris image plastic element, it is sometimes necessary to move the front cover vis-a-vis the plastic element to provide a desired complementary fit. During this step it is known that the painted iris image can smear or otherwise become distorted, rendering the iris element useless and requiring that a new iris element be painted. As mentioned briefly above, this unwanted distortion of the iris image during attachment of the cornea piece of the assembly is also known to occur when using an iris image formed by photographic technique described above, due to the interaction of solvents in the adhesive with the chemicals in the photographic film or photographic paper.

It is, therefore, desired that an iris assembly be constructed for use in a prosthetic eye device in a manner that increases the overall efficiency of making the iris assembly and the prosthetic eye device, e.g., a replacement eye. It is also desired that the iris assembly be constructed in a manner that: (1) enables use of the same in applications calling for a nonplanar fitment of a prosthetic eye device with an adjacent portion of a patient's eye or ocular implant; (2) provides a normal appearing iris from both front and side views; (3) minimizes or eliminates the potential for iris assembly delamination; (4) minimizes or eliminates the potential for unwanted distortion of the iris image during iris assembly construction; and (5) minimizes or eliminates the need to start from scratch when changing or modifying the iris image during iris assembly construction.

SUMMARY OF THE INVENTION

An iris assembly, for use with a prosthetic eye device, constructed according to the practice of this invention comprises an iris button having a frontside surface. In a preferred embodiment, the iris button is configured having a nonplanar frontside surface. An iris member is joined to the iris button frontside surface, and has an iris image disposed onto a frontside surface of the iris member. The iris member is preferably shaped to conform to the iris button, and is bonded to the iris member using a chemical agent.

In a preferred embodiment, the iris image is provided using digital image capture, enhancement, storage, and photo reproduction printing techniques, and is provided using a suitable print medium and print substrate. In a preferred embodiment, the iris image is provided by a photo reproduction process of depositing a print medium in the form of a desired ink or toner, e.g., a lightfast quality ink or toner, onto a print substrate in the form of a desired paper, e.g., a high-quality acid-free paper. Use of a paper print substrate is desired as it is malleable, thereby enabling the iris image to be configured to include multiple or variable curves without distortion. The ability to conform the iris image in this manner allows for precise custom fitting of the iris and posterior of a prosthetic eye device, comprising the same, to tissues in the patient's eye socket.

A cornea piece is made from a clear material, and is joined to the iris member's frontside surface. In a preferred embodiment, the cornea piece is joined to the iris member by using a desired adhesive solution, and curing the same at conditions of elevated temperature and pressure. Prior to joining, however, the iris member is encapsulated with a protective layer to prevent unwanted smudging or other type of distortion of the iris image that can occur during the step of joining the cornea piece. In a preferred embodiment, the iris member is encapsulated by a process of impregnating the iris member with a desired chemical agent, and then allowing the chemical agent to cure and, thereby form the protective layer.

Iris assemblies of this invention are constructed in a manner that provide a more accurate reproduction of the iris image, in a manner that is both time efficient and cost effective, when compared to conventional iris assemblies and methods for making the same. Specifically, this invention enables the iris image, or sections or parts of the same, to be stored electronically, and exactly, accurately and consistently reproduced at any time. This invention further enables portions of the iris image, or the entire iris image, to be changed, modified, altered or resized as necessary without having to start from scratch.

BRIEF DESCRIPTION OF THE DRAWINGS

These and other features and advantages of the present invention will become appreciated as the same becomes better understood with reference to the specification, claims and drawings wherein:

DETAILED DESCRIPTION

Iris assemblies of this invention are constructed using a digital image, and digital image enhancement, digital image storage, and digital photo reproduction printing techniques to create an iris image having a matching appearance of a natural eye. The iris image of this invention is provided in the form of a paper member that is specially curved and processed to prevent unwanted distortion of the iris image during further assembly steps to form an iris assembly in a manner that is both time and cost effective when compared to conventional techniques. Iris assemblies of this invention can be used with a variety of different types of prosthetic eye devices calling for a replacement iris component. Such prosthetic eye devices can be used to partially compliment or completely replace a patient's eye.

Figure 1:
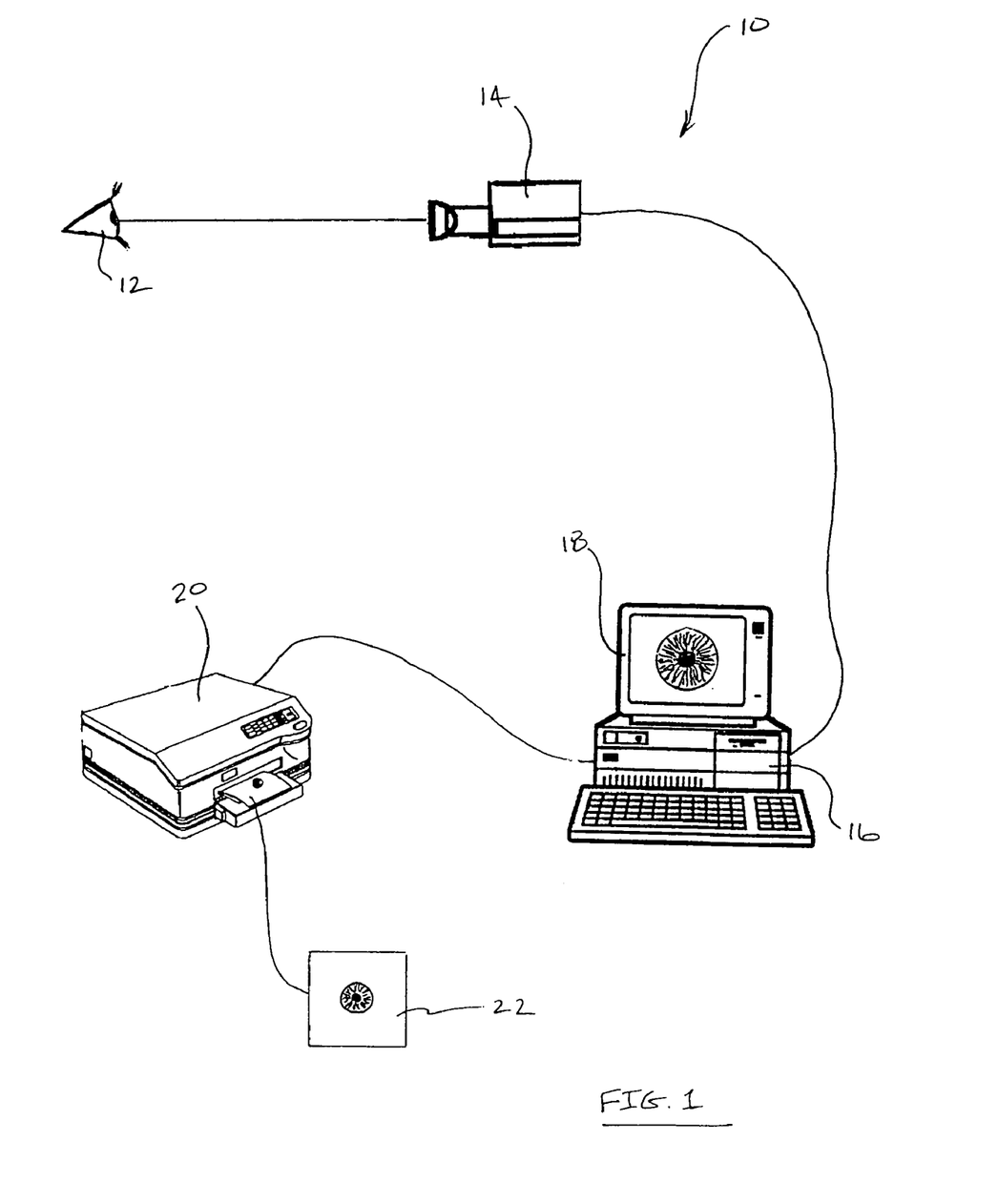
FIG. 1 is a schematic view of a system for forming an iris image used in constructing an iris assembly according to principles of this invention.

FIG. 1 illustrates a system 10 and its basic components, according to principles of this invention, for capturing and replicating an iris image of a patient's eye. The system 10 involves the use of digital technology for this purpose. A desired iris image of a patient's eye 12 is captured using a digital camera 14. Digital cameras useful for this purpose include those configured to provide either a still or video capture of the eye and, more specifically, of the iris portion of the eye. Additionally, it is desired that the digital camera be equipped to download or transfer the digital image to a signal processor, such as a computer. An example digital camera useful for this task is one made by Sony identified as Mavica-MVC-FD95.

The digital camera is used to capture the iris image, comprising the iris color and pattern of the patient's eye. The digitally-captured image is downloaded by suitable cables or other transfer means known in the art to a signal processor 16 capable of receiving the digital image. In an example embodiment, the signal processor 16 is provided in the form of a computer that processes the electronic signals provided by the camera 14. An example computer useful for this task is one made by Dell and identified as a Precision Workstation 220.

The computer is configured to include a digital image reproduction and enhancement software that enables the computer to receive the digital image from the camera and present the same onto a suitable viewing means 18, such as a video monitor. Thereby enabling one to view the results provided by the camera and/or computer. Suitable video monitors useful for this system include those conventional color computer monitors that are capable of providing a high resolution graphic image.

Example digital image reproduction and enhancement software include those capable of enabling the computer to receive the image captured by the camera, transmit the captured image to the video monitor 18, and work or adjust/enhance the image to make desired changes to the color, pattern, size, and/or shape of the iris image as may be needed for the purpose of providing an iris image that matches the appearance of the patient's eye when provided in the finished iris assembly. The digital image software also includes the ability to store the captured and worked iris image, and transmit the iris image to a suitable printer for reproduction. Suitable digital image software for this purpose include Photoshop sold by Adobe, and Corel Draw and Corel Photostyler.

Once a desired iris image is obtained on the computer 16, the iris image is sent to a suitable photo reproduction means 20, such as a printer. The printer is a color printer that can work on ink or laser technology, and one capable of providing a threshold resolution image 22 than can capture the complex color and pattern image of the iris. It is further desired that the printer be one capable of providing the iris image using a print medium and print substrate that does not present problems such as smudging and distorting during subsequent processing of the printed iris image.

It has been discovered though much experimentation that the choice of print medium, e.g., ink or toner, and the choice of print substrate, e.g., paper, that is used to capture the iris image 22 is important for helping to provide a stable, distortion resistant iris image. It is desired that the type of print medium used be one that is capable of providing a printed image having properties of extended lightfastness and improved stability, when compared to ordinary print inks or toners. In an example embodiment, the print medium is provided in the form of an ink, such as a dye ink, or a pigment ink, and the like. In a preferred embodiment, the print medium is provided in the form of a high-lightfastness color pigment ink referred to in the industry as "archival" ink.

It is desired that the type of print substrate used be one that is capable of providing properties of lightfastness and improved stability, when compared to conventional printing paper. It is also desired that the print substrate be formed from a material that permits the iris image to be shaped into a desired nonplanar configuration. In a preferred embodiment, the print substrate is provided in the form of an acid-free paper referred to in the industry as "archival" paper. It is further preferred that the paper have a flat matt surface.

Archival papers and inks are intentionally created for the purpose of providing enhanced photo reproduction image life, without unwanted fading, or distortion, on the order of 200 years. It has been discovered that the use of such ink and paper produces a printed iris image 22 that provides a level of image stability and resistance to fading, smudging, and distorting that exceeds that obtained by using conventional, i.e., nonarchival, ink and paper. In a preferred embodiment, the type of printer that is used to provide the iris image, using such archival ink and paper, is one manufactured by Epson as model number 2000P.

Using the above-described system, once an image of the patient's iris is taken and downloaded into the computer, it may or may not need working before being sent to the printer. Much depends on the capabilities of the camera, software, computer, and printer on whether the iris image as captured by the camera, processed by the computer, and printed by the printer will provide an iris image in the finished iris assembly that closely replicates the patient's iris. Therefore, it may be necessary that the iris image be worked or adjusted on the computer to make up for these potential shortcomings.

Additionally, in constructing the iris assembly of this invention, the iris image is ultimately placed behind a clear lens or cornea piece, which is also known to affect the final iris image. For example, while the printed iris image may look identical to the patient's actual iris, the printed iris image may look different, e.g., darker or lighter, from the patient's actual iris once the lens is placed over the iris image and the iris assembly is completed. Thus, the iris image can be worked, e.g., lightened or darkened, on the computer to anticipate this effect.

Once the desired iris image is printed, it may be desired to ensure that the ink used to print the iris image is fully dried or cured. In an example embodiment, the printed iris image is heat dried for a period of time. In an example embodiment, the iris image is heat dried for a period of about 30 minutes under a 100 Watt bulb. The step of heat drying operates to cure the ink in the printed image for the purpose of avoiding or preventing any unwanted smudging or distorting of the iris image during subsequent handling and/or processing.

Figure 2:
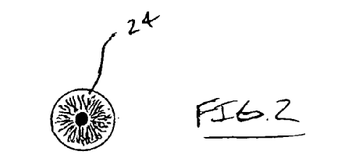
FIG. 2 is a schematic view of the iris image from FIG. 1 after it has been trimmed from the print substrate.

Once the iris image is captured, adjusted, printed, and dried according to the above-described system, it is trimmed. FIG. 2 illustrates the printed iris image of this invention after it has been trimmed along the outside border of the iris to form an iris member 24. The iris member 24 preferably comprises only the iris and pupil portions of the eye for the purpose of facilitating subsequent processing of the iris member. Because iris assemblies of this invention are being used directly to form a prosthetic eye device, the size of the iris member is to scale.

Because the human iris has a nonplanar geometry, it is desired that the iris member 24 be shaped in a manner that replicates the patent's eye. Thereby, providing an iris member that accurately replicates the natural appearance of a patient's eye. It is also desired that the iris member be shaped to have a nonplanar geometry for the purpose of configuring the iris assembly of this invention to permit proper fitment, of a prosthetic eye device comprising the same, with an adjacent portion of a patent's existing eye or ocular implant. A shaped iris member enables multiple curving of a backside surface of the iris assembly for providing precise custom fitting of the iris and posterior portion of a prosthetic eye to tissues in a patient's eye socket.

Figures 2, 3:
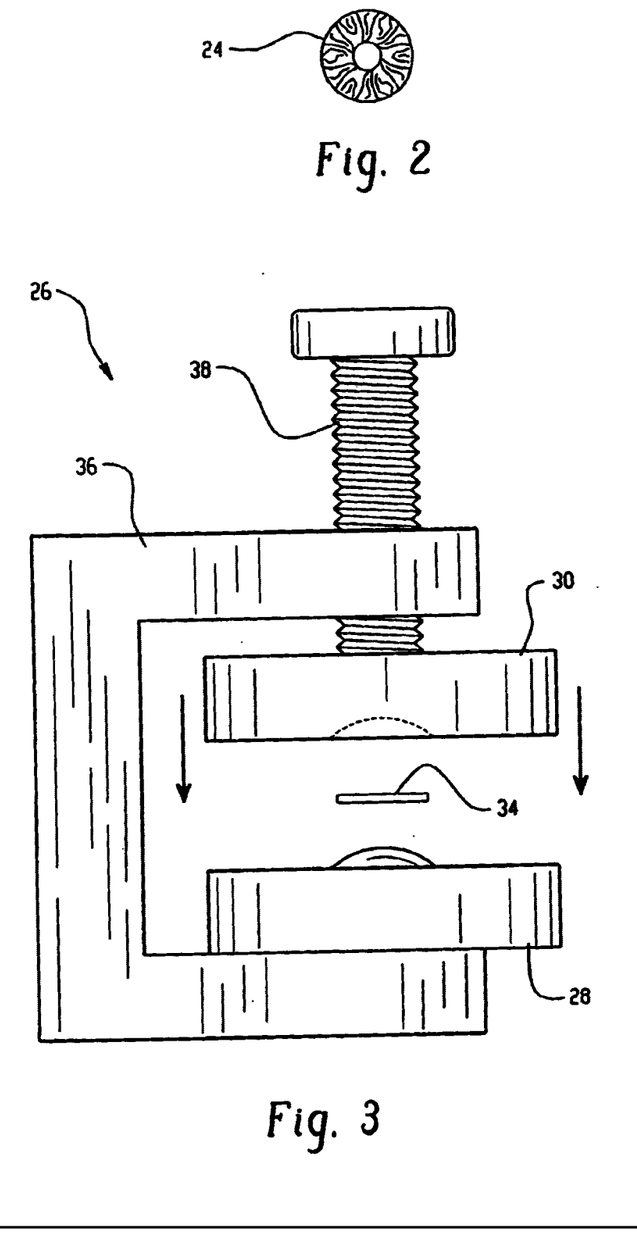
FIG. 3 is a side view of a pressing device used to shape the iris image of FIG. 2 according to principles of this invention.
Figure 3:
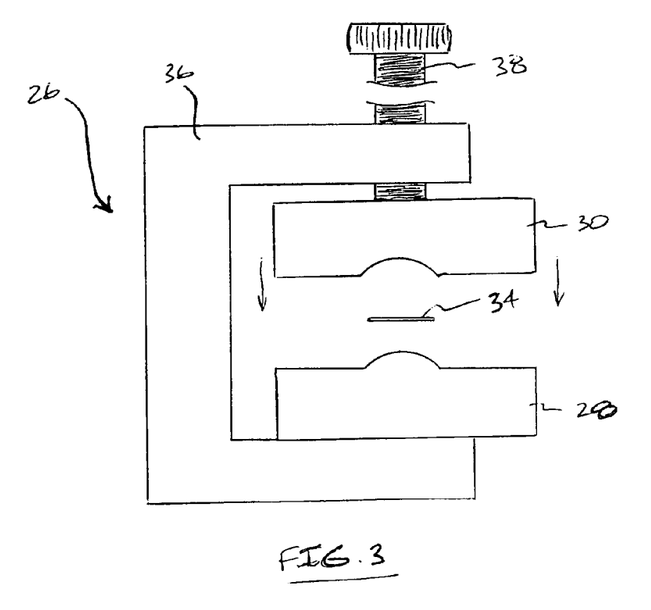

FIG. 3 illustrates a pressing means 26 useful for shaping the iris member of this invention. The pressing means can be of any form, e.g., a clamp, press, or the like, that is capable of imposing a desired shape onto the iris member. In an example embodiment, the pressing means 26 is in the form of a two-piece press assembly comprising opposed first and second members 28 and 30, each having complementary surface features configured to correspond and register with one another.

Figure 4:
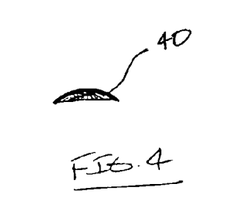
FIG. 4 is a side view of the iris image after it has been shaped.

Because the iris portion of the human eye generally has a convex shaped geometry, i.e., one defined having a radiused surface curvature, the surface features of the pressing means are configured to impose a convex shape onto the iris member 34 that is interposed therebetween. The pressing means 26 may include means for combining the first and second members together, or may be loaded into such means, e.g., in the form of a clamp 36 or the like. In an example embodiment, the first and second members 28 and 30 are loaded into the clamp 36, and a threaded clamp member 38 is turned to impose a desired pressure force between the members and onto the iris member 34. For purpose of protecting the iris image from any possible damage during this process, a piece of plastic film or the like can be used to isolate the printed surface of the iris member 34 from the second member 30. FIG. 4 illustrates the iris member 36 of this invention after it has been shaped by the above-described process. A feature of this invention is that the iris member 36 does not become significantly creased or suffer any other type of significant surface distortion during the shaping process. This is thought to be due to the use of the archival paper. Another feature of this invention is that the iris image does not become smudged or distorted during the pressing process. This is thought to be due to the use of the archival paper in combination with the archival ink, and dry heat curing of the same.

After the iris member is shaped, it is treated for the purpose of further protecting the iris image from being smudged or otherwise distorted during subsequent handling and/or processing. In an example embodiment, the shaped iris member is covered or encapsulated with a protective layer of clear material. This can be done, for example by using a preformed film or by soaking the iris member in a chemical solution and allowing the solution to cure and, thereby form the protective layer. In a preferred embodiment, the iris member is soaked with a chemical solution for a sufficient period time to impregnate the iris member with the solution. The chemical solution can be one that is chemically compatible with the materials of the iris member, and with the materials of the other contacting portions of the iris assembly, and one capable of curing to provide a crosslinked protective covering over the iris member. In a preferred embodiment, the chemical solution is a mixture of methyl methacrylic monomer and polymer that is provided in the form of a syrup-like viscus liquid.

In a preferred embodiment, the iris member is soaked in the chemical solution for a period of approximately one hour. After soaking, the iris member is heat dried for a period of time at a curing temperature, e.g., for methyl methacrylic at about 212° F. In a preferred embodiment, this curing process takes place for period of approximately one hour under a 100 Watt bulb. During the step of heat drying, it is theorized that the chemical solution undergoes chemical crosslinking reactions that operate to encapsulate the iris member and iris image, forming a clear protective covering thereover. It has been discovered through much experimentation that this step of impregnating and encapsulating the iris member is critical in protecting the iris image and, thereby preventing smudging or distorting of the iris image during subsequent processing to construct the iris assembly. Impregnation and encapsulation of the iris member also eliminates the possibility of future delamination, e.g., between the iris member and a cornea piece, that can allow in light from the side posterior of the iris assembly and cause the iris image to appear distorted.

Figures 5, 6:
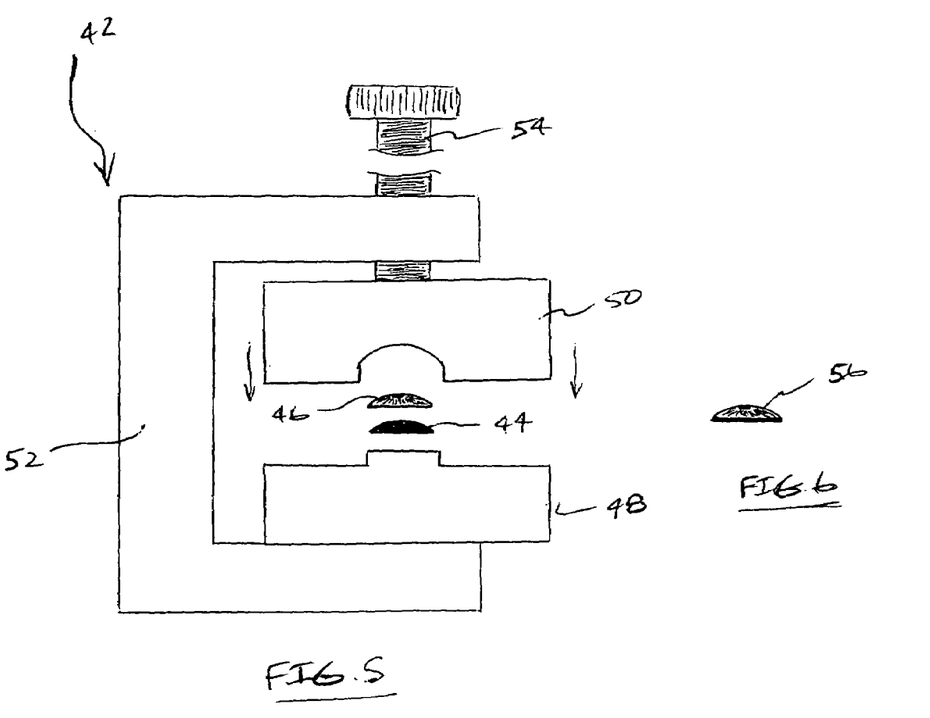
FIG. 5 is a side view of a pressing device use to combine the shaped iris image with an iris button according to principles of this invention.
FIG. 6 is a side view of the assembled shaped iris image and iris button of FIG. 5.
Figure 6:
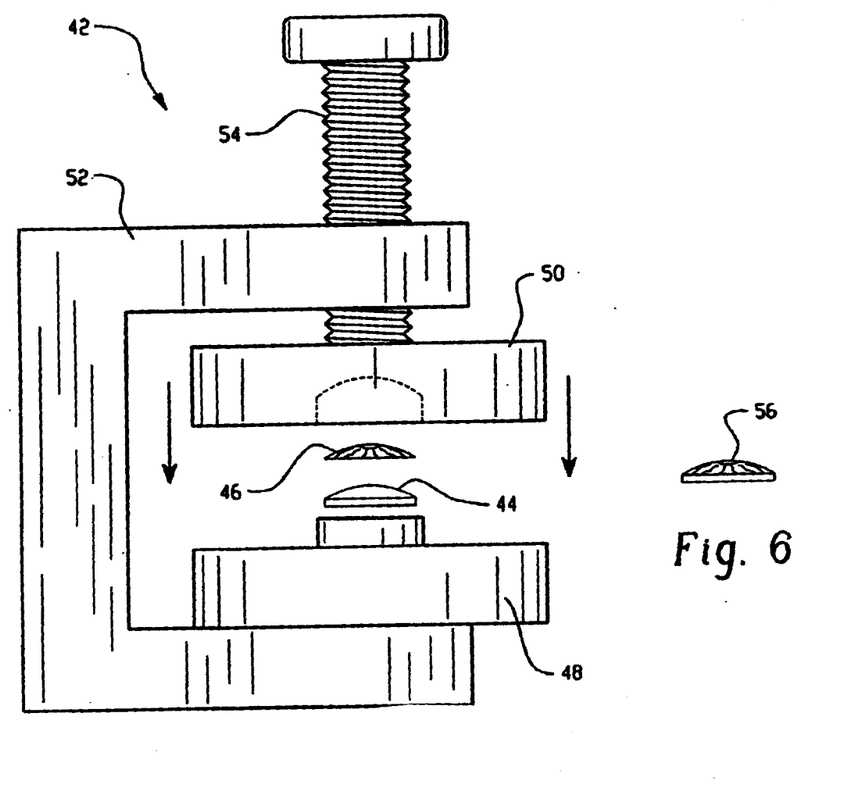

After the iris member is encapsulated, it is mounted to an iris button. FIG. 5 illustrates a pressing means 42 useful for combining an iris button 44 to a backside surface of the iris member 46. The iris button 44 is formed from a suitable rigid material, such as plastic or the like. In a preferred embodiment, the iris button is formed from the same type of material that is used to form the remaining portion of the prosthetic eye device, e.g., methyl methacrylate. The iris button has a frontside surface that is shaped to complement the backside surface of the iris member 46, e.g., that is convex shaped. The iris button 44 is sized having a diameter that is approximately that of the iris member.

In an example embodiment, the pressing means 42 can be similar to that used for the shaping step, e.g., a two-piece press assembly comprising first and second members 48 and 50. The first press assembly member 48 is configured to cooperate with a backside surface of the iris button 44, and the second press member 50 is configured to cooperate with a frontside surface of the iris member 46. In an example embodiment, the first and second members 48 and 50 are loaded into a clamp 52 having a threaded member 54 that is turned to impose a desired pressure force between the two members, thereby pressing the iris button and iris member together.

Prior to loading the iris member and iris button into the pressing means 42, an adhesive solution is placed between the adjoining surfaces of the iris member and iris button. The type of adhesive solutions useful for joining the iris member and iris button together include those having chemistries that complement the materials of, and that are capable of forming a bond between, the iris member and iris button. In an example embodiment, the adhesive solution that is used is the same as that used to encapsulate the iris member, i.e., a mixture of methyl methacrylic monomer and polymer that is provided in the form of a syrup-like viscus liquid.

The desired adhesive solution is applied both to the backside surface of the iris member and the frontside surface of the iris button. Once the adhesive solution has been applied, the iris member and iris button are placed together and are loaded into the pressing means 42. The clamp is operated to press the two press members, and the iris member and iris button, together. The clamp and press means are then exposed to an elevated temperature for the purpose of causing the adhesive solution to undergo chemical reaction to thereby bond the iris member and iris button together.

It has been discovered through much experimentation that successful bonding of the iris member and iris button is achieved under conditions of elevated temperature and, more specifically, under conditions of dry heat. In a preferred embodiment, where the adhesive solution is the methyl methacrylic monomer and polymer mixture described above, the clamp and press means is exposed to a dry heat temperature in the range of from between 195 to 205° F., for a period of approximately 35 minutes. After this period of time, the clamp and pressing means are removed from the heat and allowed to cool. FIG. 6 illustrates the bonded together iris subassembly 56, comprising the iris member and iris button. After removal from the press means, the iris subassembly 56 is cleaned by appropriate means to remove any unwanted adhesive that may have run onto the backside surface of the iris button.

Figure 7:
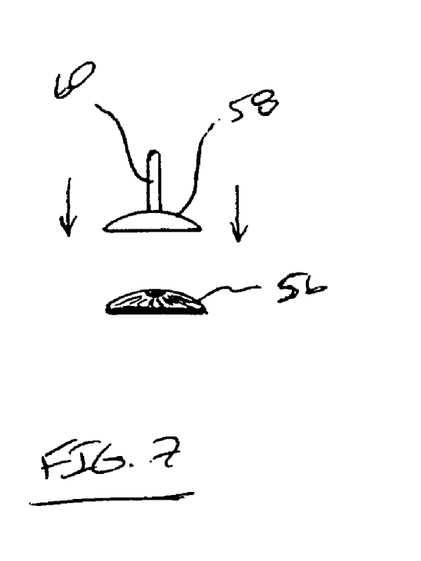
FIG. 7 is a side view of the assembled shaped iris image and iris button of FIG. 6 as combined with a cornea.

FIG. 7 illustrates the process of joining a cornea piece 58 to the iris subassembly 56. The cornea piece 58 is in the form of a clear plastic member that is configured to fit over the frontside or iris image of the iris subassembly 56, e.g., that has an adjoining concave surface. Suitable plastics useful for forming the cornea piece 58 includes those that are chemically compatible with both the iris subassembly, and the remaining portion of the prosthetic eye device. In an example embodiment, the cornea piece 58 is formed from methyl methacrylate. In the embodiment illustrated in FIG. 7, the cornea piece 58 has a projecting stem 60 that is provided for the purpose of facilitating handling of the completed iris assembly in forming the prosthetic eye device, which stem is eventually removed.

Prior to combining the two pieces, an adhesive solution is placed between the adjoining surfaces of the iris subassembly 56 and the cornea piece 58. The type of adhesive solution useful for joining the iris subassembly and cornea piece together include those having chemistries that complement the materials of, and that are capable of forming a bond between, the two members. In an example embodiment, the adhesive solution that is used is the same as that used to encapsulate the iris member, i.e., a mixture of methyl methacrylic monomer and polymer that is provided in the form of a viscus syrup-like liquid.

The desired adhesive solution is applied both to the backside surface of the cornea piece 58 and the frontside surface or iris image of the iris subassembly 56. Once the adhesive solution has been applied, the iris subassembly and the cornea piece are pressed together by hand pressure. Any adhesive solution that runs out from the two combined members, and onto the cornea piece, is cleaned away. The combined iris subassembly and cornea piece is then exposed to an elevated temperature at atmospheric pressure for the purpose of causing the adhesive solution to undergo chemical reaction to bond the iris subassembly and cornea piece together and, thereby form the completed iris assembly 62 illustrated in FIG. 8. During this process it is important that a sufficient quantity of the adhesive solution be applied to the joined together members so that a small quantity of the adhesive slips out between the two members pieces to form a seal along the common periphery.

Figure 8:
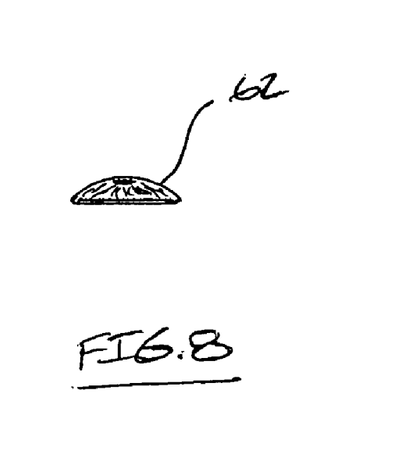
FIG. 8 is a side view of the assembled iris image, iris button, and cornea, forming the iris assembly of this invention.

It has been discovered through much experimentation that successful bonding is achieved under conditions of pressure elevated temperature and, more specifically, under conditions of dry heat. In a preferred embodiment, where the adhesive solution is the methyl methacrylic monomer and polymer mixture described above, the combined iris subassembly and cornea piece is exposed to pressure and a dry heat temperature in the range of from between 195 to 205° F., for a period of approximately 30 minutes. After this period of time, the newly-formed iris assembly 62 is removed from the heat and allowed to cool.

The iris assembly is next cleaned using appropriate means, for the purpose or removing any excess adhesive solution that may have run onto nonjoined surfaces of the combined members, and polished using appropriate means. The resulting iris assembly is then ready for combining with the other portions of the prosthetic eye device to form the finished product.

Key features of this invention include, but are not limited to: (1) the use digital image capture, enhancement, storage, and photo replication technologies to produce an iris image, thereby improving reproduction accuracy and saving time and cost when compared to the conventional method of partially or entirely hand painting the iris image; (2) the use of a conformable and print receptive substrate for capturing the iris image, and the subsequent curing of the printed image, to provide an iris image that is resistant to smudging and/or distortion during subsequent handling or processing; (3) the use of a chemical agent to impregnate and encapsulate the iris image after it has been printed, thereby forming a protective cover or film over the iris image to protect the iris image and further prevent smudging or distorting of the image during subsequent processing; (4) the use of a non-planar iris member for the purpose of both accurately replicating the geometry of a human iris, and enabling precise fitment of a prosthetic eye device comprising the same; and (5) the use of a special chemical agent in adhering the iris member to the iris button, and adhering the iris subassembly to the cornea lens, and the use of elevated pressure and dry heat to perfect bonding of the same.

Although, limited embodiments iris assemblies and methods of making the same of this invention have been described and illustrated herein, many modifications and variations will be apparent to those skilled in the art. Accordingly, it is to be understood that within the scope of the appended claims, iris assemblies of this invention may be embodied other than as specifically described herein.

What is claimed is:

1. A method for forming an iris assembly for use with a prosthetic eye device, the method comprising the steps of:
    taking a digital image of an iris and transferring the image to a computer;
    creating a photo reproduction of the image by printing the iris image onto a substrate;
    encapsulating the iris image with a polymeric material; and
    bonding the encapsulated iris image to an iris button, on a backside surface of the iris image, and to a clear cornea piece, on an opposite frontside surface of the iris image.

2. The method as recited in claim 1 wherein before the step of printing, enhancing the digital iris image using the computer.

3. The method as recited in claim 1 wherein before the step of encapsulating, shaping the printed iris image into a nonplanar configuration.

4. The method as recited in claim 1 wherein the step of printing the iris image comprises forming the iris image by depositing archival ink onto a sheet of archival paper.

5. The method as recited in claim 1 wherein the step of encapsulating comprises impregnating the iris image in a chemical solution and curing the chemical solution using elevated temperature conditions.

6. The method as recited in claim 5 wherein the chemical solution comprises methyl methacrylic.

7. The method as recited in claim 1 wherein the step of bonding comprises placing an amount of adhesive solution between the iris image and iris button, and joining the two together under conditions of elevated pressure and dry heat.

8. The method as recited in claim 7 wherein the step of bonding comprises placing an amount of adhesive solution between the iris image and cornea piece, and joining the two together under conditions of elevated pressure and dry heat.

9. A method for forming an iris assembly for use with a prosthetic eye device, the method comprising the steps of:

capturing a digital image of an iris and transferring the captured image to a computer;

enhancing the digital image using the computer and printing an iris image onto a paper substrate;

shaping the printed iris image into a nonplanar configuration;

encapsulating the shaped iris image with a polymeric material; and bonding the shaped and encapsulated iris image to an iris button, on a backside surface of the iris image, and to a clear cornea piece, on an opposite frontside surface of the iris image.

10. The method as recited in claim 9 wherein the step of encapsulating comprises impregnating the iris image in a chemical solution and curing the chemical solution using elevated temperature conditions.

11. The method as recited in claim 10 wherein the chemical solution comprises methyl methacrylic.

12. The method as recited in claim 11 wherein the step of bonding comprises placing an amount of adhesive solution between the iris image and iris button, and joining the two together under conditions of elevated pressure and temperature.

13. The method as recited in claim 12 wherein the step of bonding comprises placing an amount of adhesive solution between the iris image and cornea piece, and joining the two together under conditions of elevated pressure and temperature.

* * * * *

UNITED STATES PATENT AND TRADEMARK OFFICE
CERTIFICATE OF CORRECTION

PATENT NO. : 7,029,608 B1
APPLICATION NO. : 10/192958
DATED : April 18, 2006
INVENTOR(S) : Frederick R. Lewis et al.

It is certified that error appears in the above-identified patent and that said Letters Patent is hereby corrected as shown below:

The sheets of drawings consisting of figures 1-8 should be deleted to appear as per attached figures 1-8.

The title page should be deleted to appear as per attached title page.

Signed and Sealed this

Tenth Day of October, 2006

JON W. DUDAS
*Director of the United States Patent and Trademark Office*

United States Patent
Lewis et al.

(10) Patent No.: US 7,029,608 B1
(45) Date of Patent: Apr. 18, 2006

(54) IRIS ASSEMBLY FOR A PROSTHETIC EYE DEVICE

(76) Inventors: Frederick R. Lewis, 1360 Bluesail Cir., Westlake Village, CA (US) 91361; Carole Lewis Stolpe, 4239 Navajo St., Toluca Lake, CA (US) 91602

(*) Notice: Subject to any disclaimer, the term of this patent is extended or adjusted under 35 U.S.C. 154(b) by 546 days.

(21) Appl. No.: 10/192,958

(22) Filed: Jul. 11, 2002

(51) Int. Cl.
*B29D 11/00* (2006.01)

(52) U.S. Cl. .................................. 264/1.7; 156/61
(58) Field of Classification Search ............... 623/4.1, 623/6.64; 156/61; 264/1.1, 1.7, 1.32
See application file for complete search history.

(56) References Cited

U.S. PATENT DOCUMENTS

| | | | |
|---|---|---|---|
| 2,497,873 A * | 2/1950 | Erpf ......................... | 623/6.64 |
| 5,863,363 A * | 1/1999 | Sankey ..................... | 156/61 |
| 6,746,120 B1 * | 6/2004 | Broderick et al. ....... | 351/177 |
| 6,811,461 B1 * | 11/2004 | Maddocks et al. ....... | 446/392 |
| 2004/0233383 A1 * | 11/2004 | Sandler et al. ........... | 351/163 |
| 2005/0067725 A1 * | 3/2005 | Hsu ........................... | 264/1.32 |
| 2005/0272833 A1 * | 12/2005 | Doshi ....................... | 523/160 |

* cited by examiner

*Primary Examiner*—Suzette J-J Gherbi
(74) *Attorney, Agent, or Firm*—Eley Law Firm Co.; James R. Eley; Michael A. Forhan (57) ABSTRACT

An iris assembly of this invention comprises an iris button having a frontside surface. An iris member is joined to the iris button frontside surface and has an iris image disposed thereon. The iris image is provided using digital image capture, storage, enhancement, and printing techniques, and is provided onto a suitable substrate. A cornea piece is made from a clear material, and is joined to the iris member frontside surface. Prior to joining, the iris member is encapsulated with a clear protective film thereover that operates to protect the iris image from unwanted smudging or other type of distortion during the step of joining the cornea piece. Iris assemblies of this invention are constructed in a manner that provide a more accurate reproduction of the iris image, in a manner that is both time efficient and cost effective, when compared to conventional iris assemblies and methods for making the same.

13 Claims, 4 Drawing Sheets